(12) United States Patent
Fujimoto et al.

(10) Patent No.: US 7,966,091 B2
(45) Date of Patent: Jun. 21, 2011

(54) AUTOMATIC THIN-SECTION SLIDES MANUFACTURING SYSTEM AND METHOD

(75) Inventors: Koji Fujimoto, Chiba (JP); Tetsumasa Ito, Chiba (JP); Tatsuya Miyatani, Chiba (JP)

(73) Assignee: Seiko Instruments Inc. (JP)

( * ) Notice: Subject to any disclaimer, the term of this patent is extended or adjusted under 35 U.S.C. 154(b) by 221 days.

(21) Appl. No.: 12/223,406

(22) PCT Filed: Feb. 7, 2007

(86) PCT No.: PCT/JP2007/052058
§ 371 (c)(1),
(2), (4) Date: Oct. 17, 2008

(87) PCT Pub. No.: WO2007/094205
PCT Pub. Date: Aug. 23, 2007

(65) Prior Publication Data
US 2010/0030364 A1 Feb. 4, 2010

(30) Foreign Application Priority Data
Feb. 13, 2006 (JP) .................................. 2006-035053

(51) Int. Cl.
*G06F 19/00* (2011.01)
(52) U.S. Cl. ..................................... 700/117; 435/40.52
(58) Field of Classification Search .................. 700/117; 435/29, 40.52; 523/168; 83/155
See application file for complete search history.

(56) References Cited

U.S. PATENT DOCUMENTS

| | | | |
|---|---|---|---|
| 3,552,247 A | 1/1971 | Pickett | 83/24 |
| 3,832,923 A | 9/1974 | Lassmann et al. | 83/16 |
| 4,317,401 A | 3/1982 | Disharoon | 83/856 |
| 5,609,083 A | 3/1997 | Persson | 83/14 |
| 5,713,255 A | 2/1998 | Izvozichikov et al. | 83/24 |
| 7,179,424 B2 * | 2/2007 | Williamson et al. | 422/102 |
| 2003/0022271 A1 | 1/2003 | Voneiff et al. | 435/40.52 |
| 2003/0120633 A1 * | 6/2003 | Torre-Bueno | 707/1 |
| 2003/0215936 A1 | 11/2003 | Kallioniemi et al. | 435/287.1 |
| 2005/0059155 A1 | 3/2005 | Graupner et al. | 436/43 |
| 2005/0235542 A1 | 10/2005 | Metzner et al. | 42/24 |
| 2007/0141711 A1 * | 6/2007 | Stephens et al. | 436/43 |
| 2008/0235055 A1 * | 9/2008 | Mattingly et al. | 705/3 |
| 2008/0305515 A1 * | 12/2008 | Burgart et al. | 435/40.52 |
| 2010/0184127 A1 * | 7/2010 | Williamson et al. | 435/40.52 |

FOREIGN PATENT DOCUMENTS

| | | |
|---|---|---|
| JP | 06323967 | 11/1994 |
| JP | 08035921 | 2/1996 |
| JP | 2003014597 | 1/2003 |
| JP | 2004028910 | 1/2004 |

* cited by examiner

*Primary Examiner* — Albert Decady
*Assistant Examiner* — Dave Robertson
(74) *Attorney, Agent, or Firm* — Adams & Wilks

(57) ABSTRACT

Thin-section slide samples are manufactured from respective embedding blocks containing a biological sample and held in an embedding cassette having imprinted thereon individual data. The embedding cassette is transported to a cutting position where an embedding block is cut into sheet-like thin sections, and the individual data is read out. Each of thin sections is flattened and transferred onto a substrate to form a thin-section slide sample. A memory part stores the individual data read out and a condition table into which is input manufacturing conditions for manufacturing the thin sections. Thereafter, it is evaluated whether or not each of the thin sections is prepared in accordance with the manufacturing conditions input into the condition table.

20 Claims, 8 Drawing Sheets

AUTOMATIC THIN-SECTION SLIDES MANUFACTURING SYSTEM AND METHOD

CROSS-REFERENCE TO RELATED APPLICATIONS

This application is a U.S. national stage application of International Application No. PCT/JP2007/052058, filed Feb. 7, 2007, claiming a priority date of Feb. 13, 2006, and published in a non-English language.

BACKGROUND OF THE INVENTION

1. Field of the Invention

The present invention relates to an automatic thin-section slides manufacturing system and an automated thin-section slides manufacturing method which automatically manufactures thin-section slides for use in physicochemical experiments and microscopic observations.

2. Background Art

Microtome has been known as a conventional tool for use in general in preparing thin section slide samples for physicochemical experiments and microscopic observations. The thin-section slides are prepared by fixing thin sections about several micrometers (for instance, from 3 µm to 5 µm) in thickness on a substrate such as a glass slide. A generally employed method for preparing a thin section sample using a microtome is described below.

An embedded block is prepared by first subjecting a formalin-fixed biological sample taken out from living bodies, laboratory animals, and the like to paraffin substitution, and then solidifying the periphery thereof with paraffin to prepare a solid block. Then, preliminary cutting is carried out by setting the embedded block in a microtome, i.e., a thin sectioning apparatus especially designed for this purpose. By preliminary cutting, the surface of the embedded block is smoothed, and the biological sample, which is intended to be subjected to the experiment or observation, is brought into a state that is exposed to the surface.

Upon completion of preliminary cutting, main cutting is carried out. In this process step, the cutting blade of the microtome slices the embedded block to provide ultra-thin sections at the predetermined thickness. Thin sections having the intended surface can be obtained in this manner. In such a case, more accurate observation data can be made available by slicing the embedded block as thin as possible in the order of microns, since the thickness of the thin section can be brought near to that of a living cell. Accordingly, it is required to manufacture thin sections as thin as possible. The main cutting step is carried out continuously until thin sections are obtained for the desired number.

Subsequently, thin sections thus obtained are flattened in the flattening process. More specifically, because the thin sections obtained by the main cutting are sliced so thinly, they are apt to be wrinkled or curled (U-shaped). Thus, flattening step is necessary to remove the wrinkles or curls from the thin sections.

In general, flattening is performed by using water and hot water. Firstly, the thin section obtained by main cutting is released in water to set a float. In this manner, large wrinkles or curls of the thin section can be removed while preventing the paraffin, which contains embedded therein the biological sample, from sticking with each other. The thin section is then floated in hot water. The wrinkles which remained unremoved by the water flattening or the deformation which has generated during cutting can be removed from the thin section, because the thin sections are more easily extended in hot water.

After finishing hot flattening, the thin section is mounted on a substrate by scooping it onto a substrate such as a slide glass. If flattening is insufficient at this point, the substrate having the thin section mounted thereon is wholly placed on a hot plate and the like to further apply heat. In this manner, the thin section can be further flattened.

Finally, the substrate having mounted thereon the thin section is dried by placing it inside an oven. By drying, the water adhered to the thin section during flattening evaporates, and the thin section is fixed on the substrate.

As a result, a thin section slide sample can be obtained. The thin section slide samples thus manufactured are mainly used in the biological and medical fields.

Recently, needs for understanding comprehensively and histologically the gene or protein expression are increasing, not only in the diagnostic approach employed heretofore for distinguishing normal/abnormal cells from their shapes, but also in due course of the recent progress in genome science. Accordingly, it is required to efficiently and homogeneously manufacture a larger number of thin section slide samples. However, since most of the process steps described above require highly sophisticated technique and experience, skilled operators had to engage manually in the processes, and hence, much time and labor were consumed on the processes.

Accordingly, in order to overcome such inconveniences even if only a little, there is provided a thin section sample manufacturing apparatus which carries out a part of the processes above (reference can be made to, for instance, Patent Literature 1).

The thin section sample manufacturing apparatus automatically carries out a process step of manufacturing the thin sections by cutting the already set embedded block, a step of transporting the thus manufactured thin section on a carrier tape to transfer it on a slide glass, and a step of performing flattening by transporting the thin section together with the slide glass to the flattening apparatus.

In accordance with the thin section sample manufacturing apparatus, favorable thin section slide samples can be manufactured while reducing the burden of the operator and preventing human-induced errors from occurring.

On the other hand, as an apparatus for manufacturing thin section slide samples by utilizing a microtome, there is also provided an apparatus which relates an embedded block with the thin section slide samples manufactured from the corresponding embedded block.

Although there are several apparatuses of this type, there is known an apparatus, for example, which reads the identification information (an identification information imprinted in advance) of the cassette having mounted thereon the embedded block, and which then allocates the thin section to be mounted by displaying the thus read identification information on the substrate such as the slide glass and the like. (For instance, reference can be made to Patent Literature 2)

Further, there is known another apparatus, which reads the data (which is imprinted in advance) of the cassette on which an embedded block is mounted and the identification information (which is data imprinted in advance) of the substrate such as a slide glass on which the thin section is to be mounted, and queries whether the both data match with each other or not (reference can be made to, for instance, Patent Literature 2).

At any rate, any apparatus above enables relating the embedded block with the corresponding substrate. Thus, an operator conducts the operation step of mounting the thin section sliced by using the microtome on the substrate while appropriately applying the flattening process and the like. As a result, the thin section slide samples can be related to the embedded block.

[Patent Literature 1] Published Japanese patent application 2004-28910

[Patent Literature 2] Published Japanese translation of a PCT patent application 2005-509154

[Patent Literature 3] Published Japanese patent application 2005-91358

However, the apparatuses known heretofore as described above still suffered problems as follows.

First, the thin section sample manufacturing apparatus described in the Patent Literature 1 automatically manufactures thin section slide samples from a single embedded block; however, when thin section slide samples are successively manufactured from plural embedded blocks while efficiently exchanging the blocks, there may be cases in which thus manufactured plural thin section slide samples lose the track from which embedded block they had been manufactured. In particular, when the embedded biological samples are organs which look similar to each other in shapes, difficulties are found in distinguishing them from each other. Accordingly, there had been an inconvenience in relating the embedded block with the thin section slide samples.

Particularly in the embedded blocks, it is required to observe the expression of all the major organs of the animal under consideration, and this requires thinly cutting 20 pieces or more embedded blocks per one animal sample. In practice, because the experimental results are statistically processed, the population size of the embedded blocks is generally increased during the experiments, and may easily reach several hundreds. Accordingly, the number of thin section slide samples also became huge as to make them prone to cause the problems stated above.

As a result, it was found impossible to conduct an accurate quality control, and this affected the reliability of the observation using the thin section slide samples.

On the other hand, the apparatuses disclosed in Patent Literatures 2 and 3 cannot automatically manufacture thin section slide samples, and the operator himself or herself had to flatten the thin sections sliced with the microtome, followed by mounting them on a substrate. Thus, not only the operators suffered large burden, but also the process consumed much time and labor.

Moreover, because the thin section slide samples had to be manufactured manually by the operators, even if the substrate should be related in advance with the embedded block, human-induced errors occurred during the process such as the flattening step of the thin sections and the step of mounting the thin section on a substrate, resulting in cases in which the thin section slide samples were incompletely related to the embedded blocks.

SUMMARY OF THE INVENTION

The present invention has been made in the light of the above circumstances, and an objective of the invention is to provide an automatic thin-section slides manufacturing system and an automated thin-section slides manufacturing method, which automatically manufacture required number of thin section slide samples from plural embedded blocks while reducing the burden of the operators, and at the same time, completely relate the manufactured thin section slide samples to the original embedded blocks to enable quality control at high precision.

In order to solve the above problems, the present invention provides the following solutions.

According to an aspect of the invention, there is provided an automatic thin-section slides manufacturing system for manufacturing thin section slide samples respectively from a plurality of embedded blocks containing a biological sample embedded therein with an embedding medium and held in an embedded cassette having imprinted thereon an individual data including at least an identification number, which comprises: a first transportation unit which is capable of transporting an arbitrarily selected embedded cassette from the plural embedded cassettes to the cutting position; a cutting unit which, after the embedded cassette is transported to the cutting position, cuts the embedded block to provide sheet-like thin sections at a predetermined thickness; a readout unit which reads out the individual data when the embedded cassette is transported to the cutting position; a flattening unit for flattening the thin section, which comprises a storage tank containing a liquid stored therein; a second transportation unit which transports the thin sections cut out by the cutting unit to the storage tank and sets them a float on the liquid surface; a transfer unit which prepares the thin section slide samples by transferring the thin section flattened in the flattening unit onto a substrate; a control unit which comprises a memory part for memorizing the individual data read out by the readout unit; and a recording unit which records the memorized individual data on the substrate upon receiving a command from the control unit.

According to another aspect of the invention, there is provided an automated thin-section slides manufacturing method for manufacturing thin-section slides respectively from a plurality of embedded blocks containing a biological sample embedded therein with an embedding medium and held in an embedded cassette having imprinted thereon an individual data including at least an identification number, by cutting out sheet-like thin sections and at the same time transferring the thin section on a substrate, which comprises: a first transportation step for transporting the embedded cassette arbitrarily selected from the plurality of embedded cassettes to a cutting position; a reading step for reading the individual data from the embedded cassette transported to the cutting position; a cutting step for cutting out a sheet-like thin section by cutting it out at a predetermined thickness from the embedded block transported to the cutting position; a second transportation step for transporting the cut thin section to a storage tank filled with a liquid and setting the cut thin section a float on the liquid surface for starting flattening; a transfer step for transferring the flattened thin section on the substrate to manufacture the thin section slide sample; and a recording step for storing the individual data in the memory part and recording the stored individual data on the substrate.

In the automatic thin-section slides manufacturing system and the automated thin-section slides manufacturing method according to the invention, an individual data containing at least a specific identification number is imprinted in advance to the embedded cassette holding therein the embedded block. In this manner, the embedded blocks held in the embedded cassettes are surely distinguished from each other.

Subsequently, on starting the operation, the control unit controls the first transportation unit to conduct the first transportation step which comprises transporting one embedded cassette, which has been arbitrarily selected from plural embedded cassettes, to the cutting position. In this instance, the operator may pass the embedded cassette manually to the first transportation unit, or pick up the embedded cassette in which the first transportation unit is set at a predetermined position.

Once the embedded cassette is transported to the cutting position, the readout unit conducts the reading step to read out the individual data of the embedded cassette, and outputs the read out individual data to the control unit. By this reading step, the embedded block that has been sent out first can be identified. Furthermore, the control unit stores the thus sent out individual data in the memory part.

Further, when the embedded cassette is transported to the cutting position, the cutting unit conducts the cutting step to prepare thin sections, in which the embedded block being held in the embedded cassette is cut (sliced) into sheet-like thin sections at a predetermined thickness (for example, at a ultrathin thickness of 5 μm). The second transportation unit conducts the second transportation step in which the thus cut thin sections are transported to the storage tank in the flattening unit, in which a liquid such as water is stored, and are floated on the surface of water (liquid) to initiate flattening. By the flattening unit, the thin sections attain a flattened state because the wrinkles and the curls that have generated during cutting are removed. After flattening, the transfer unit runs the transfer step in which the thin sections floated on the surface of the water are transferred onto a substrate such as a slide glass and fixed. Thus, thin section slide samples having thin sections fixed on the substrate are manufactured as a result.

Then, either after or before the transfer step, the recording step is effected in which the recording unit records the individual data that have been memorized in the memory part onto the substrate in accordance with the instructions given by the control unit. In this manner, the manufactured thin section slide samples achieve a state in which the same individual data that have been described in advance on the embedded cassette is recorded thereon. In other words, the thin section slide sample attain a sate as such that they are related to the embedded blocks held in the embedded cassettes.

Furthermore, after required amount of thin section slide samples is manufactured from the first transported embedded block, the control unit returns back the embedded cassette so that the next embedded cassette maybe transported to the cutting position. That is, the first transportation step is repeated for the next embedded block.

Then, by repeating each of the process steps described above, the desired amount of thin sections are cut out from each of the plural embedded blocks to automatically manufacture the thin section slide samples. Thus, differing from the conventional ones, the system not only reduces the burden of the operator, but also shortens the operation time. Furthermore, the generation of human-induced errors can also be avoided.

In particular, as described above, the same individual data as that of the embedded cassette are recorded on the thin section slide samples thus manufactured so as to completely relate samples to the original embedded block. Accordingly, quality control of high precision can be effected because the operator can easily and surely check which automatically manufactured thin section slide sample comes from which embedded block.

As described hereinbefore, the automatic thin-section slides manufacturing system and the automated thin-section slides manufacturing method of the present embodiment automatically manufacture required number of thin section slide samples from plural embedded blocks while reducing the burden of the operators, and at the same time, completely relate the manufactured thin section slide samples to the original embedded blocks to enable control at high precision.

Furthermore, in accordance with another aspect of the invention, there is provided the automatic thin-section slides manufacturing system as above, in which the control unit issues an instruction to the recording unit when a plurality of the thin section slide samples are prepared from the same embedded block, so that the memory part stores the data in such a state that branch numbers for respectively distinguishing the thin section slide samples are each added to the individual data and that the data are each recorded on the substrates.

Further, according to a yet other aspect of the invention, there is provided the automated thin-section slides manufacturing method as above, wherein in the recording step, when a plurality of the thin section slide samples are prepared from the same embedded block, the recording unit stores the data in such a state that branch numbers for respectively distinguishing the thin section slide samples are each added to the individual data, and the data are each recorded on the substrates.

In the automatic thin-section slides manufacturing system and the automated thin-section slides manufacturing method according to the invention, when plural thin sections are cut out from a single embedded block, for instance five thin sections are cut out to manufacture five thin section slide samples, the control unit memorizes the read-out individual data with five branch numerals attached thereto. In this manner, the fact that five thin section slide samples were manufactured from the same embedded block is surely memorized.

Then, the control unit sends out instructions to the recording unit so that each of the five substrates on which five thin sections are each transferred may have recorded thereon the respective individual data with a branch number attached thereto. As a result, even in the case plural thin section slide samples are manufactured from the embedded block having the same individual data, the samples can be clearly distinguished from each other. Thus, this realizes a more accurate quality control.

In accordance with a yet other aspect of the invention, there is provided the automatic thin-section slides manufacturing system as described above, in which the recording unit prints the individual data on the substrate by irradiating laser radiation.

In accordance with another aspect of the invention, there is provided the automated thin-section slides manufacturing method as described above, wherein in the recording step, the individual data are printed on the substrate by irradiating laser radiation.

In the automatic thin-section slides manufacturing system and the automated thin-section slides manufacturing method according to the invention, the recording unit irradiates a laser radiation to the substrate during the recording step to print the individual data. In this manner, clear printing can be obtained without applying any external force to the substrate, thereby preventing warping, deformation, and the like from occurring on the substrate. Specially mentioned in this case is that it enables the use of an organic solvent such as xylene, alcohol, and the like in the later process steps, because the characters printed by the laser radiation cannot be erased even if the substrate should be immersed in the organic solvent. Thus, an extremely reliable thin section slide sample can be manufactured with higher quality.

According to a still other aspect of the invention, there is provided the automatic thin-section slides manufacturing system as above described, in which the recording unit is a thermal transfer printer, which prints the individual data by transferring them on the substrate.

According to another aspect of the invention, there is provided the automated thin-section slides manufacturing method as above described, wherein in the recording step, the individual data are transferred to be printed on the substrate by a thermal transfer printer.

In the automatic thin-section slides manufacturing system and the automated thin-section slides manufacturing method according to the invention, during the recording step, the thermal transfer printer directly transfers the individual data onto the substrate for printing. In particular, because the individual data is printable on the substrate by applying heat and thereby sublimating the ink, the printing density can be finely set to provide a clear printing. Accordingly, easily discernible thin section slide samples can be obtained with high quality.

According to a further aspect of the invention, there is provided the automatic thin-section slides manufacturing system as above, in which the recording unit includes a thermal transfer printer which transfers the individual data to an exclusive use paper, and the exclusive use paper printed with the thermal transfer printer is attached to the substrate.

According to a further other aspect of the invention, there is provided the automated thin-section slides manufacturing method as above, wherein in the recording step, the individual data are transferred to be printed on an exclusive use paper by a thermal transfer printer, and the printed exclusive use paper is attached to the substrate.

In the case of carrying out the recording step with the automatic thin-section slides manufacturing system and the automated thin-section slides manufacturing method according to the invention, the thermal transfer printer prints the individual data on an exclusive use paper. Subsequently, the recording unit attaches the exclusive use paper having printed thereon the individual data to the substrate. In this manner, the individual data can be recorded on the substrate. In particular, since the individual data are printable on the exclusive use paper by applying heat and thereby sublimating the ink, the print density can be finely set to obtain a clear print. Accordingly, an easily discernible thin section slide sample can be manufactured with high quality.

According to a yet other aspect of the invention, there is provided the automatic thin-section slides manufacturing system as one of the above-stated automatic thin-section slides manufacturing systems, in which the system further comprises a cabinet for storing plural embedded cassettes in such a manner that they can be put in and taken out; and the control unit controls the first transportation unit in such a manner that an arbitrarily selected embedded cassette is taken out from the cabinet and transported to the cutting position, and after the necessary amount of thin sections are cut out, that the embedded cassette is returned back to the cabinet to take out the next embedded cassette.

According to another aspect of the invention, there is provided the automated thin-section slides manufacturing method as one of the above-stated automated thin-section slides manufacturing methods, wherein, in the first transportation step, the arbitrarily selected embedded cassette is taken out from the cabinet having previously stored therein plural embedded cassettes in such a manner that they can be put in and taken out, and transported to the cutting position, and after the necessary amount of thin sections are cut out, the embedded cassette is returned back to the cabinet to take out again the next embedded cassette.

In the automatic thin-section slides manufacturing system and the automated thin-section slides manufacturing method according to the invention, a cabinet is provided so that the operator may store plural embedded cassettes therein in advance. Thus, in the first transportation step, the first transportation unit takes out one embedded cassette stored in the cabinet and transports it to the cutting position. Then, after cutting out the desired number of thin sections from the embedded block held in the embedded cassette to manufacture the thin section slide samples, the first transportation unit returns the embedded cassette back to its original position in the cabinet and takes out the next selected embedded cassette from the cabinet and transports it to the cutting position.

Thus, the exchange operation of the embedded cassettes can be efficiently and automatically carried out by the operator by just storing plural embedded cassettes in advance inside the cabinet. Accordingly, not only the burden of the operator can be reduced, but also the operation time can be shortened.

According to a still other aspect of the invention, there is provided the automatic thin-section slides manufacturing system as one of the above-stated automatic thin-section slides manufacturing systems, wherein the transfer unit comprises a storage rack for storing plural thin section slide samples, and the control unit controls the transfer unit in such a manner that the manufactured thin section slide samples are stored in the storage rack.

Further according to another aspect of the invention, there is provided the automated thin-section slides manufacturing method as one of the above-stated automated thin-section slides manufacturing method, wherein, in the transfer step, the manufactured thin section slide sample is stored in a storage rack capable of storing plural section slides.

In the transfer step of the automatic thin-section slides manufacturing system and the automated thin-section slides manufacturing method according to the invention, the transfer unit automatically stores the thin section slide samples which have completed with the recording of the individual data in the storage rack. Accordingly, the burden of the operator can be further reduced and the operation time can be still shortened. Furthermore, since the finished thin section slide samples are stored in the exclusive use rack, the thin section slide samples can be handled more easily thereafter.

DESCRIPTION OF THE PREFERRED EMBODIMENTS

An embodiment of the automatic thin-section slides manufacturing system and the automated thin-section slides manufacturing method according to the invention is described below by making reference to FIGS. 1 to 7. The automatic thin-section slides manufacturing system automatically manufactures thin section slide samples by cutting out thin sections from a plurality of embedded blocks containing biological samples embedded therein in an embedding medium and held in an embedded cassette, and by then transferring the thin sections on the substrates.

In the present embodiment, the explanation is made by referring as examples on the biological tissues collected from laboratory animals such as a mouse and a monkey.

First, explanations are made on the embedded cassette and the embedded block.

Figure 1:
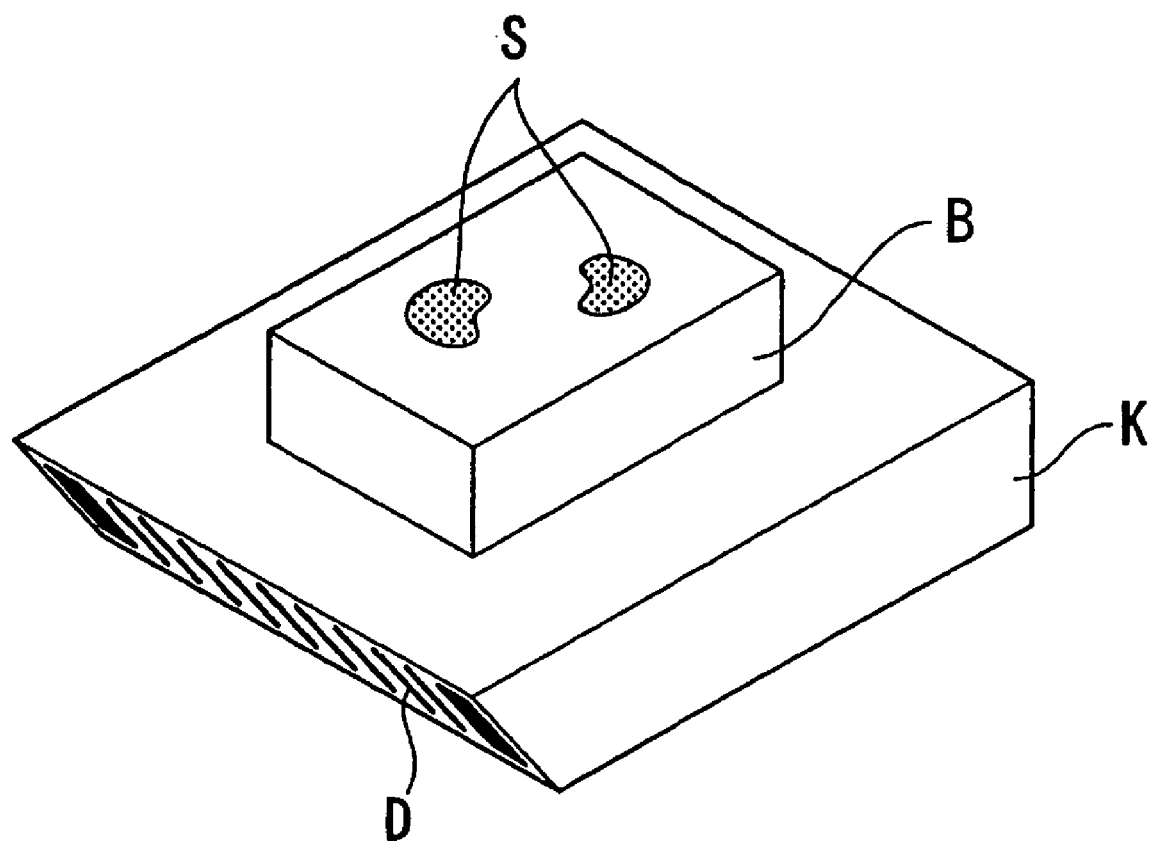
FIG. 1 shows an oblique view of an embedded cassette and an embedded block for use in an automatic thin-section slides manufacturing system according to the invention.

Referring to FIG. 1, an embedded block B is prepared by paraffin-substituting water inside a formalin-fixed biological tissue S, and then solidifying the periphery with an embedding medium such as paraffin to obtain the block. In this manner, the biological tissue S is maintained embedded inside paraffin. Furthermore, the embedded block B is held inside an embedded cassette K provided in a box-like shape. Depending on the type of the laboratory animal, sex of the laboratory animal, the type of the organs of the laboratory animal, and the like, plural types of biological tissues S are prepared and each embedded to separately provide the embedded blocks B.

The embedded cassette K is made, for example, from plastics resistant to organic solvents and the like, and an inclined plane is provided to a part thereof. Thus, an individual data D which includes an identification number (serial number) for identifying the individual sample and the data of the holding embedded block B are printed in advance on the inclined plane. The data for the embedded block B includes, for instance, the data showing from which laboratory animal the biological tissue S was collected, the data showing the sex of the laboratory animal, and the data showing from which organ of the laboratory animal the tissue was collected.

Accordingly, by referring to the individual data D, the plural embedded cassettes K can be each distinguished from each other, and the type of the embedded block B held therein can be specified.

Then, the automatic thin-section slides manufacturing system according to the present embodiment is described below.

Figure 2:
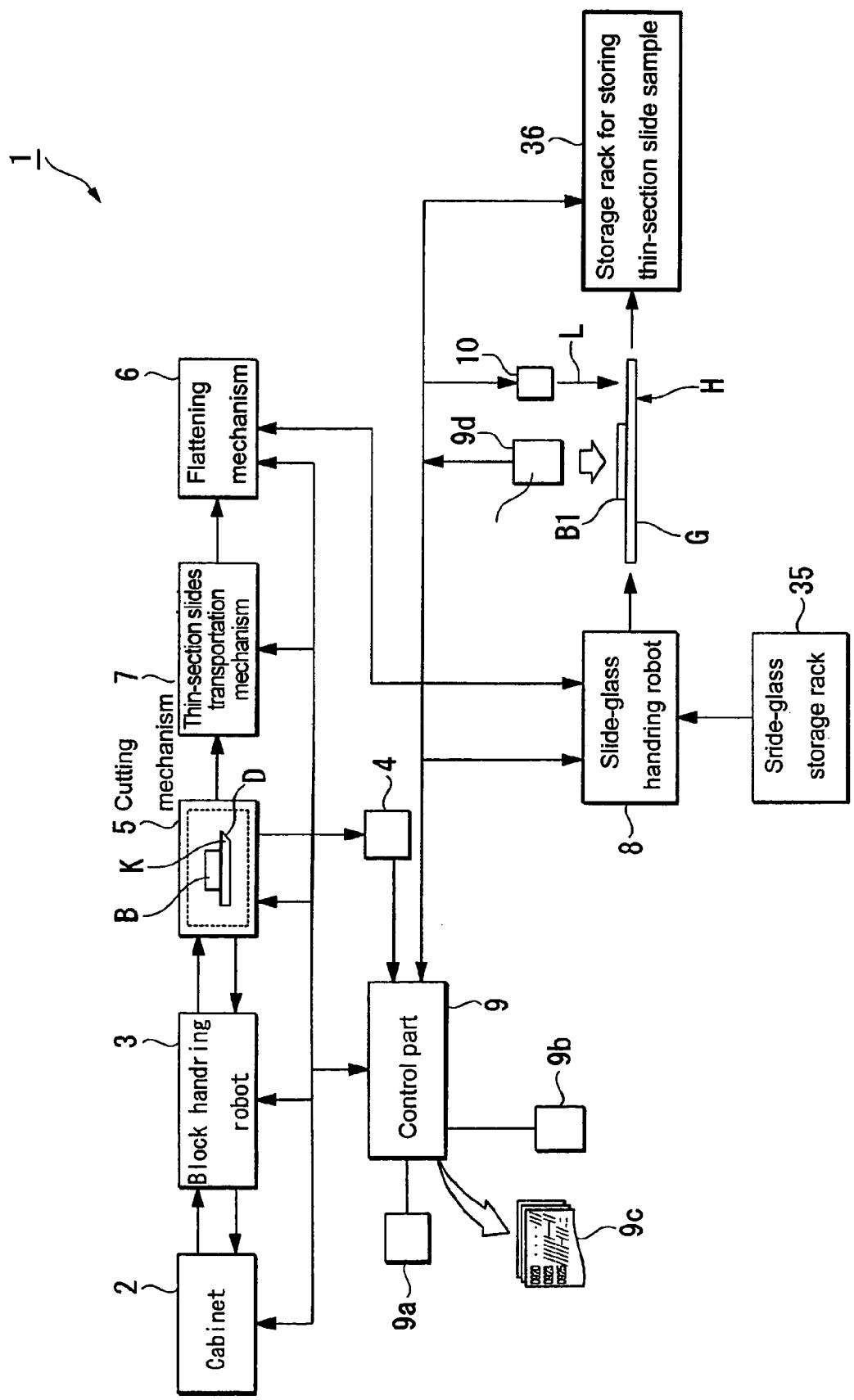
FIG. 2 is a block diagram showing the constitution of an automatic thin-section slides manufacturing system according to an embodiment of the invention.

Referring to FIG. 2, the automatic thin-section slides manufacturing system 1 according to the embodiment comprises a cabinet 2 for storing plural embedded cassettes K in such a manner that they can be put in and taken out; a block handling robot (a first transportation unit) 3 which is capable of putting in and taking out a single selected embedded cassette K from the cabinet 2, and transporting the selected embedded cassette K to the cutting position P; a readout part (readout unit) 4 to read out the individual data D when the embedded cassette K is transported to the cutting position P; a cutting mechanism (cutting unit) 5 which, after the embedded cassette K is transported to the cutting position P, cuts the embedded block B at a predetermined thickness to cut out sheet-like thin sections B1; a flattening mechanism (flattening unit) 6 equipped with a water tank (storage tank) 28 containing water (liquid) W1 stored therein, which flattens the thin sections B1; a thin-section transportation mechanism (a second transportation unit) 7, which transports the thin section B1 cut out by the cutting mechanism 5 to the water tank 28 and sets it a float in the water surface (liquid surface); a slide glass handling robot (transfer unit) 8 which transfers the flattened thin section B1 onto a slide glass (substrate) G to manufacture a thin section slide sample H; a control part (control unit) 9 which totally controls each of the components and equipped with a memory part (memorizing part) 9a for memorizing the individual data D read out by the reading part 4; and a recording part (recording unit) 10 which records on the slide glass G the individual data D, which was memorized according to the instructions given by the control part 9.

Figure 3:
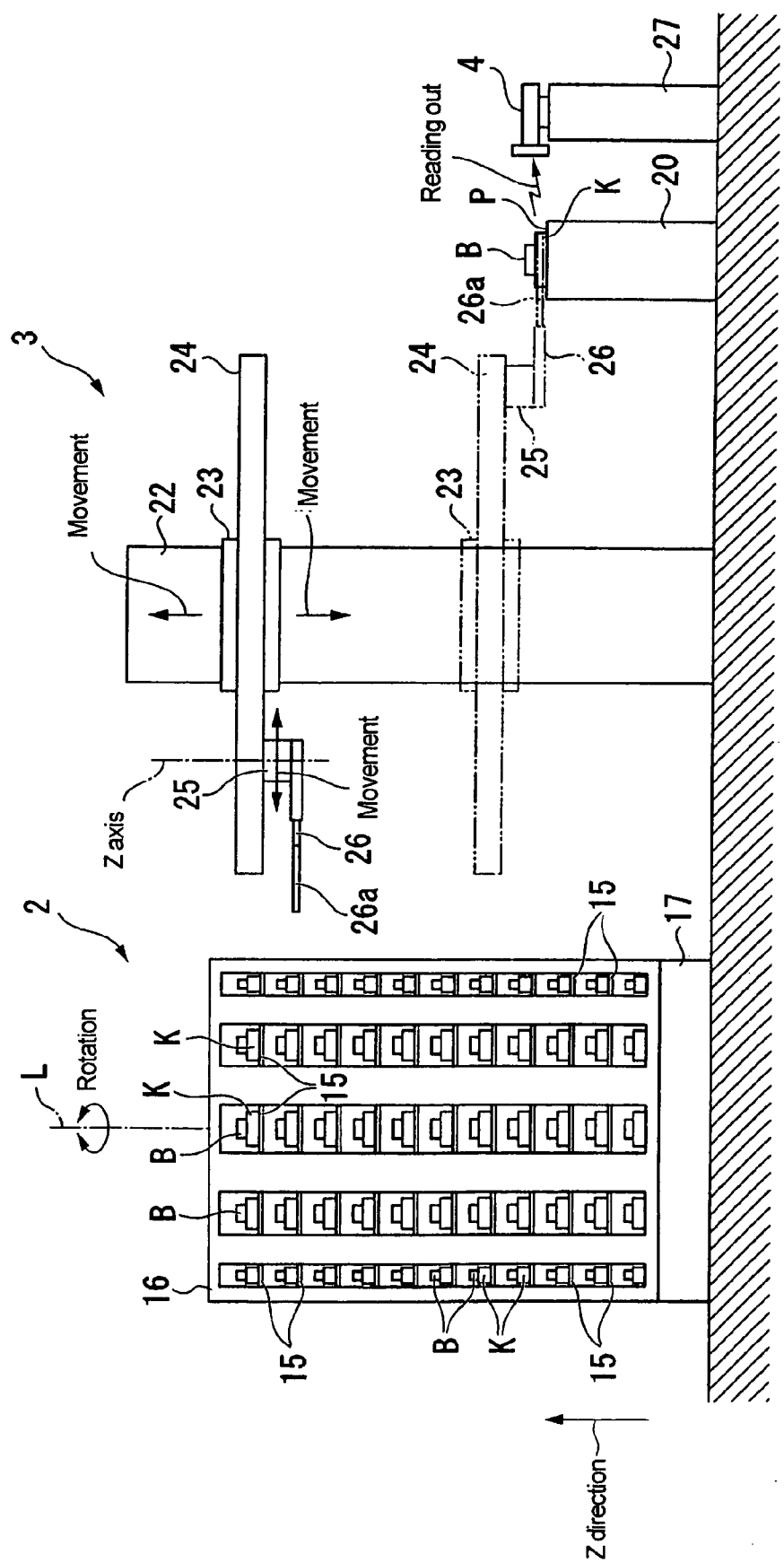
FIG. 3 shows a side view of the cabinet and the block handling robot shown in FIG. 2.
Figure 4:
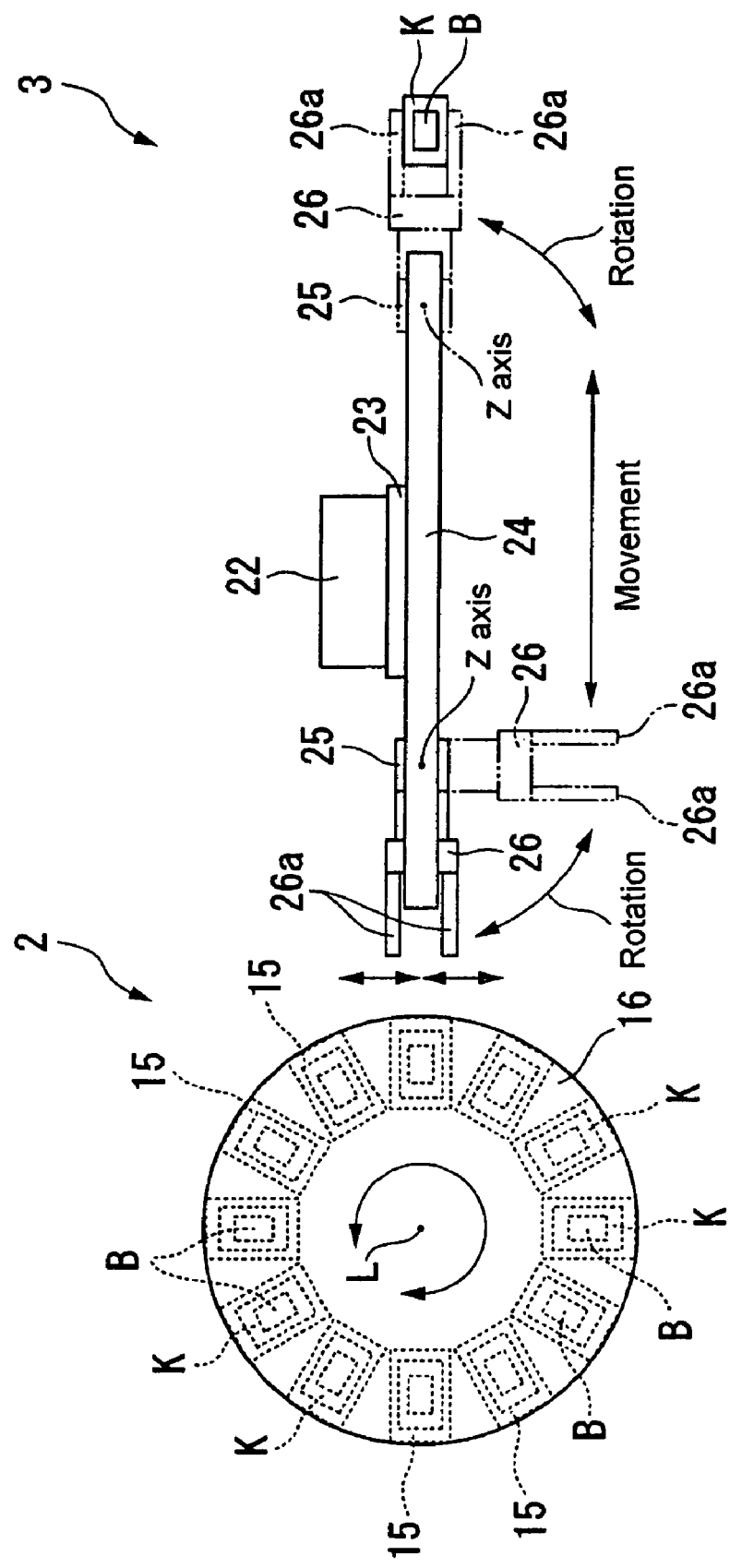
FIG. 4 shows an upper plan view of the cabinet and the block handling robot shown in FIG. 3.

Referring to FIGS. 3 and 4, the cabinet 2 as described above comprises plural storage racks 15 for divided storage of the embedded blocks B fixed on the embedded cassettes K, and a rotating body 16 which comprises the plural storage racks 15 provided on the outer peripheral plane thereof, which is set freely rotatable around the rotation axis L and whose rotation is controlled by the control part 9.

The rotating body 16 according to the present embodiment is provided as a cylinder having the axis of rotation L in the center thereof, and is fixed on a rotating stage 17 which is rotated by a driving source not shown, such as a motor. The control part 9 controls the movement of the driving source. In this manner, the rotating body 16 is controlled by the control part 9 such that it may rotate in the arbitrary direction and speed of rotation.

Then, the storage racks 15 are evenly disposed around the outer periphery of the rotating body 16; for instance, 120 storage racks are formed in total. That is, 10 racks are formed at a predetermined interval along the Z direction, i.e., the direction along the axis of rotation L; by taking these 10 racks as a unit line, 12 lines are each formed every 30 degrees around the axis of rotation L taken as the center.

Figure 5:
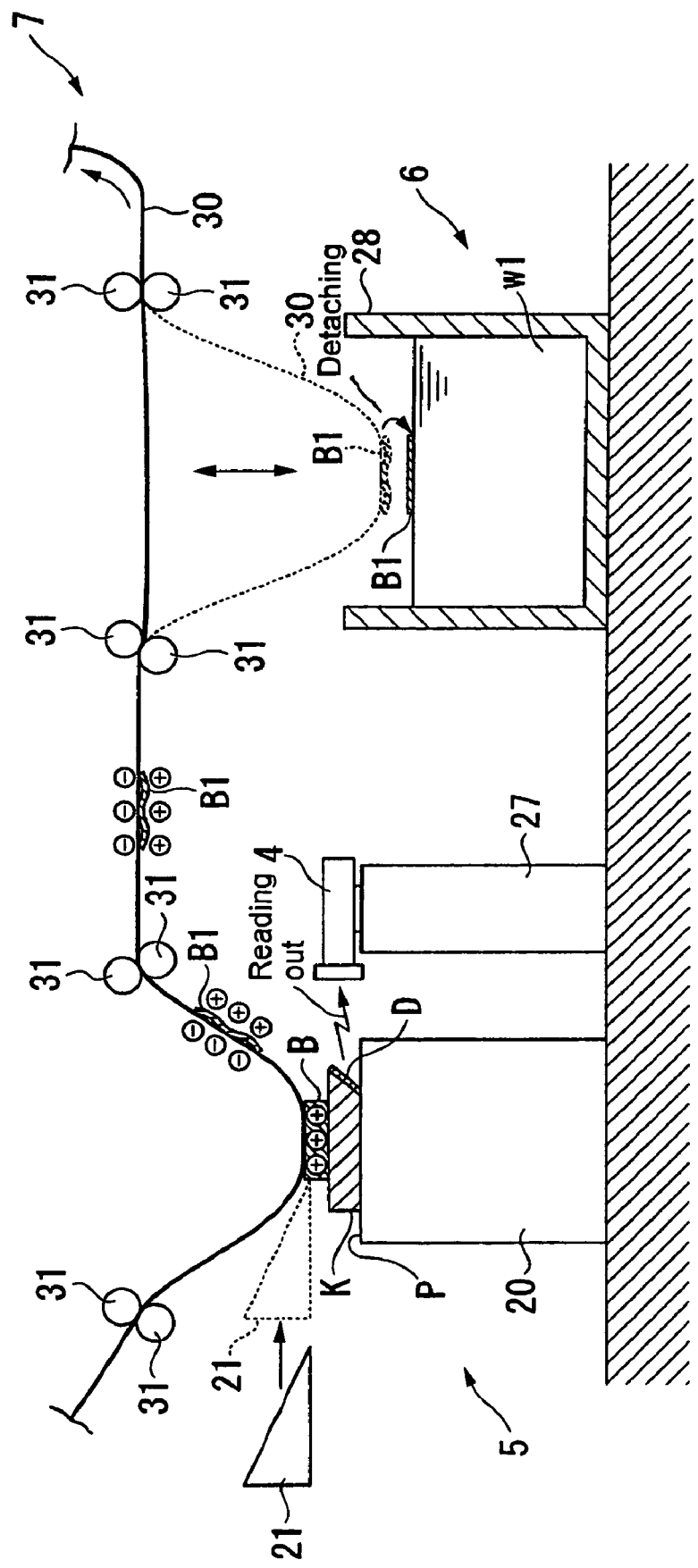
FIG. 5 shows a side view of a cutting unit, a thin sections transportation unit, a recording unit, and a flattening unit shown in FIG. 2.

Referring to FIG. 5, the cutting mechanism 5 is equipped with a block fixing table 20 for mounting and fixing thereon the embedded cassette K, which is located at a position distant from the cabinet 2 with a predetermined distance taken between, and with a cutting blade 21 which makes sliding operation on the embedded blocks B held in the mounted and fixed embedded cassettes K.

The cutting blade 21 is set as such that it may make a sliding operation at a predetermined speed and cutting angle by a driving mechanism not shown in the figure. The block fixing table 20 is set as such that it would elevate the embedded block B from the cutting plane every predetermined height in accordance with the sliding operation of the cutting blade 21. In this manner, the embedded block B can be cut at a predetermined thickness by the cutting blade 21 to cut out the thin sections B1. That is, the upper surface of the block fixing table 20 corresponds to the cutting position P. Furthermore, the embedded block B that is mounted and fixed on the block fixing table 20 is set as such that it may be positive charged by a not shown electrifying device.

In the present embodiment, it is so constituted that the cutting blade 21 makes a sliding operation on the block fixing table 20 to cut the embedded block B, but the invention is not only limited to this case. For instance, the cutting mechanism may be so constituted that the cutting blade 21 is fixed, while the block fixing table 20 is moved with respect to the fixed cutting blade 21 to cut the embedded block B. Furthermore, the cutting mechanism 5 may be constituted as such that both the cutting blade 21 and the block fixing table 20 may be moved relative to each other to cut the embedded block B.

Furthermore, as shown in FIGS. 3 and 4, a Z-axial guide rail 22, which is extended along the Z direction, is provided between the cabinet 2 and the block fixing table 20. A lifting stage 23 that is movable along the Z-axial guide rail 22 is installed in the Z-axial guide rail 22. A horizontal guide rail 24, which is extended in the horizontal direction, is installed to the lifting stage 23. Furthermore, similar to the Z-axial guide rail 22, a horizontal stage 25 that is movable along the horizontal guide rail 24 is provided to the horizontal guide rail 24. The horizontal stage 25 not only moves along the horizontal direction, but is provided rotatable around the Z-axis as shown in FIG. 4.

Furthermore, the horizontal stage 25 is provided with a clamping robot 26 equipped with a pair of arms 26a, which are disposed in parallel with each other and with a predetermined distance taken between them, with the distance being set freely changeable. Thus, by properly operating the lifting stage 23, the horizontal stage 25, and the clamping robot 26, one of the embedded blocks B kept in the storage rack 15 and stored in the cabinet can be taken out from or put into the storage rack 15.

That is, by moving the horizontal stage 25 and the lifting stage 23 while keeping the embedded cassette K, which holds the embedded block B, clamped with a pair of arm 26a, the embedded blocks B can be taken out from and put into the storage rack 15. Furthermore, by properly operating the lifting stage 23 and the horizontal stage 25 with the embedded cassette K kept clamped, the cassette can be mounted on the block fixing table 20 which corresponds to the cutting position P. These lifting stage 23, horizontal stage 25, and the clamping robot 26 are driven by a motor not shown that is controlled by the control part 9.

The Z-axial guide rail 22, the lifting stage 23, the horizontal guide rail 24, the horizontal stage 25, and the clamping robot 26 constitute the above-stated block handling robot 3. Further, as shown in FIGS. 3 and 5, a fixing table for the readout part 27, which is provided at an approximately the same height as the block fixing table 20, is placed neighbored to the block fixing table 20, and a readout part 4 is provided on the fixing table for the readout part 27. The readout part 4 optically reads out the individual data D printed on the inclined slope of the embedded cassette K when the embedded cassette K is transported to the cutting position P. The readout part 4 furthermore outputs the readout individual data D to the control part 9.

Referring then to FIG. 5, a water tank 28 is provided neighbored to the fixing table for readout part 27. The water tank 28 constitutes a part of the flattening mechanism 6 which flattens the thin section B1 that has been cut out by the cutting mechanism 5 by making use of surface tension.

To the upper side of the block fixing table 20 and the water tank 28 is provided a carrier tape 30 which is negatively charged in advance by a not shown electrifying device. The carrier tape 30 is fed in the direction from the block fixing table 20 to the water tank 28 by using a guide roller 31 and a not shown tape driving mechanism.

When the embedded cassette K is mounted on the block fixing table 20, the carrier tape 30 is set as such that its plane may be brought into contact with the surface of the embedded block B, and when it reaches the upper plane of the water tank 28, it is loosened so that it may contact the surface of the water W1 that is reserved inside the water tank 28.

In this manner, the thin section B1 cut out by the cutting mechanism 5 is electrostatically adsorbed to the lower plane of the carrier tape 30, and is transported to the water tank 28 together with the movement of the carrier tape 30 while maintaining in the adsorbed state. Then, the thin section B1 is released from the carrier tape 30 and set a float on water W1 at the point it reaches to the upper part of the water tank 28, where the carrier tape 30 is loosened and immersed in water W1.

The carrier tape 30, the guide roller 31, and the tape driving mechanism constitute the thin-section transportation mechanism 7.

Figure 6:
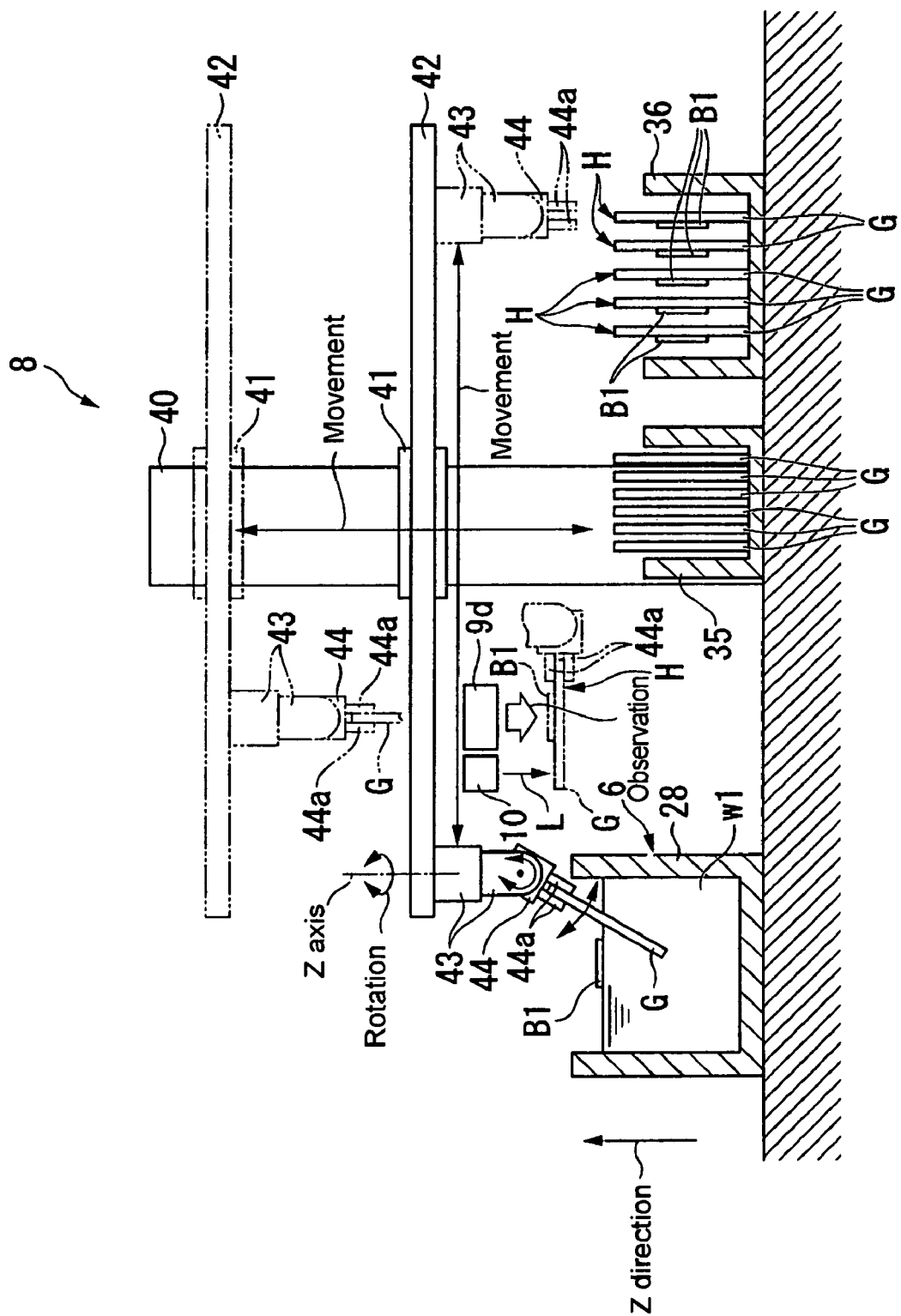
FIG. 6 shows a side view of a slide glass handling robot shown in FIG. 2.

Referring to FIG. 6, a slide glass storage rack 35 for storing in advance plural unused slide glasses G and a storage rack 36 for storing plural thin section slide samples H (storage rack), which are slide glasses G having transferred thereon the thin sections B1, are sequentially provided to the neighbor of the water tank 28.

Furthermore, similar to the block handling robot 3, a Z-axial guide rail 40 extended along the Z direction is provided between the water tank 28 and the storage rack 36 for the thin section slide samples. A lifting stage 41 capable of moving along the Z-axial guide rail 40 is attached to the Z-axial guide rail 40. A horizontal guide rail 42, which extends along the horizontal direction, is provided to the lifting stage 41. Furthermore, a horizontal stage 43, which is set movable along the horizontal guide rail 42, is attached to the horizontal guide rail 42. The horizontal stage 43 is not only movable along the horizontal direction, but is rotatable around the Z-axis.

Furthermore, to the horizontal stage 43 is attached a slide-glass clamping robot 44 in such a manner that it may rotate monoaxially around an axis orthogonal to the Z direction. Similar to the clamping robot 26, the slide-glass clamping robot 44 is equipped with a pair of arms 44a, which are disposed in parallel with each other and with a predetermined distance taken between them, with the distance being set freely changeable.

Thus, by properly functioning each of the lifting stage 41, the horizontal stage 43, and the slide-glass clamping robot 44, an unused slide glass G is clamped, and the already flattened thin section B1 floating in the water tank 28 is transferred onto the clamped slide glass G to manufacture a thin section slide sample H. Furthermore, thus manufactured thin section slide samples H can be stored inside the storage rack 36 for thin section slide samples. The details are described later hereafter.

The Z-axial guide rail 40, the lifting stage 41, the horizontal guide rail 42, the horizontal stage 43, and the slide-glass clamping robot 44 constitute the slide-glass handling robot 8.

The control part 9 described above entirely controls each of the components above. For instance, the block handling robot 3 is so controlled that it may take out an arbitrarily selected embedded cassette K from the cabinet 2 and transport it to the cutting position P, and after the required number of thin sections B1 are cut out from the embedded block B, it returns the embedded cassette K to the cabinet 2 to take out the next embedded cassette K.

Further, the slide-glass handling robot 8 is so controlled that the manufactured thin section slide samples H may be sequentially stored inside the storage rack 36 for thin section slide samples.

The control part 9 memorizes the individual data D sent from the readout part 4 in the memory part 9a, and, at the same time, issues instructions to the recording part 10 to record the individual data D on the slide glass G onto which the thin section B1 is transferred.

The recording part 10 is, for instance, a laser marker which irradiates a laser radiation L onto the slide glass G to print the individual data D in accordance with the instruction given by the control part 9. Furthermore, as shown in FIG. 6, the recording part 10 is located between the water tank 28 and the storage rack 36 for the thin section slide samples, so that the printing should be performed before the slide-glass handling robot 8 stores the thin section slide samples into the storage rack 36.

In this instance, the printing onto the slide glass G may be carried out first so that the thin sections B1 set a float on the water plane may be transferred thereafter, or the thin section slide samples H may be prepared first by transferring the thin sections B1 on the slide glass G followed by the printing.

Referring to FIG. 2, the control part 9 according to the present embodiment has, in addition to the memory part 9a as described above, a condition table 9b, in which the conditions for manufacturing the thin section slide samples H are input in advance for each of the plural embedded cassettes K. Thus, the control part 9 specifies the type of the transported embedded cassette K in accordance with the individual data D for the embedded cassette K that has been read at the readout part 4, and, at the same time, relates the individual data D to the condition table 9b. Thus, the constituents are entirely controlled so that the manufacturing process should be conducted in conformity with the manufacturing conditions set for the embedded cassette K.

More specifically, the manufacturing conditions refer to the cutting conditions and the flattening conditions, and these cutting and flattening conditions are input beforehand into the condition table 9b. The cutting conditions are those which determine at least one of the following conditions on cutting the embedded block B with the cutting mechanism 5, i.e., the thickness of the thin section B1, the cutting speed, or the cutting angle on cutting. The flattening conditions are those which determine at least one of the following conditions on flattening the thin section B1 by floating it on water W1, i.e., the temperature of water W1 and the time duration of floating. The manufacturing conditions includes, in addition to the cutting conditions and flattening conditions as above, the minimum required number of the thin section slide samples H that should be manufactured, which depends on the type of the embedded block B.

Then, the control part 9 determines those conditions in accordance with the condition table 9b depending on the type of the embedded cassette K that has been specified from the individual data D, and controls each of the constituents so that the thin section slide samples H may be manufactured under the thus determined conditions and number of samples.

The control part 9 furthermore memorizes the aforementioned manufacturing conditions (cutting conditions, flattening conditions, and the number of manufactured samples) at the same time the readout individual data D of the embedded cassette K is memorized to prepare an operation log (operation table) 9c. That is, an operation log 9c is prepared, which simultaneously memorizes the identification number of the embedded cassette K that has been transported to the cutting position P, the data showing the type of the embedded block B (i.e., the type of the biological tissue S), and the manufacturing conditions that have been determined from the condition table 9b.

Additionally, as shown in FIGS. 2 and 6, the control part 9 according to the present embodiment is equipped with an evaluating part 9d in which the thin section B1 transferred onto the slide glass G is observed and evaluated whether it is prepared in accordance with the manufacturing conditions as determined in the condition table 9b or not, and the result evaluated by the evaluating part 9d is attached to the individual data D to be memorized in the memory part 9a. In this manner, the actual results of manufacturing are memorized in the operation log 9c. The evaluating part 9d evaluates the thin section B1 by, for instance, optical observation, in which the shape and the surface conditions and the like are evaluated. Furthermore, the thin section slide samples H that are evaluated as conforming at the evaluating part 9d are recorded at the recording part 10.

In the case the sample is evaluated to be defective by the evaluating part 9d, the control part 9 controls each of the components in such a manner that a thin section B1 is cut out again from the same embedded block B to manufacture the thin section slide sample H, and that the evaluating part 9d conducts the reevaluation.

However, it is set as such that the control part 9 allows the evaluating part 9d to re-evaluate up to a predetermined times (N times), and if the re-evaluation times exceeds the predetermined value, the re-manufacturing of the thin section slide sample H from the same embedded block B is stopped thereafter. At the same time, this event is memorized in the memory part 9a.

Then, the automated thin-section slides manufacturing method using the above constituted automatic thin-section slides manufacturing system 1 is described below for manufacturing desired amount of thin section slide samples H, each from a plurality of different types of embedded blocks B and according to their manufacturing conditions.

The automated thin-section slides manufacturing method according to the present embodiment comprises a first transportation step in which one embedded cassette K, which is selected from a plurality of divided embedded cassettes set inside plural storage racks 15 and provided inside a cabinet 2, is taken out from the cabinet and transported to a cutting position P; a reading step for reading out the individual data D from the embedded cassette K transported to the cutting position P; a cutting step in which a thin section B1 is cut out at a predetermined thickness from the embedded block B transported to the cutting position P; a second transportation step in which the cut thin section B1 is transported to the water tank 28 and is set a float on the surface of the water to initiate flattening; a transfer step in which the flattened thin section B1 is transferred on a slide glass G to manufacture a thin section slide sample H; and a recording step in which the read out individual data D is memorized in the memory part 9a after the reading step, and the memorized individual data D is recorded on the slide glass G.

Furthermore, in the automated thin-section slides manufacturing method according to the present embodiment, the type of the embedded cassette K is specified according to the individual data D, and related to the condition table 9b, so that the process steps after the reading step are carried out according to the manufacturing conditions related to the thus transported embedded cassette K.

Figure 7:
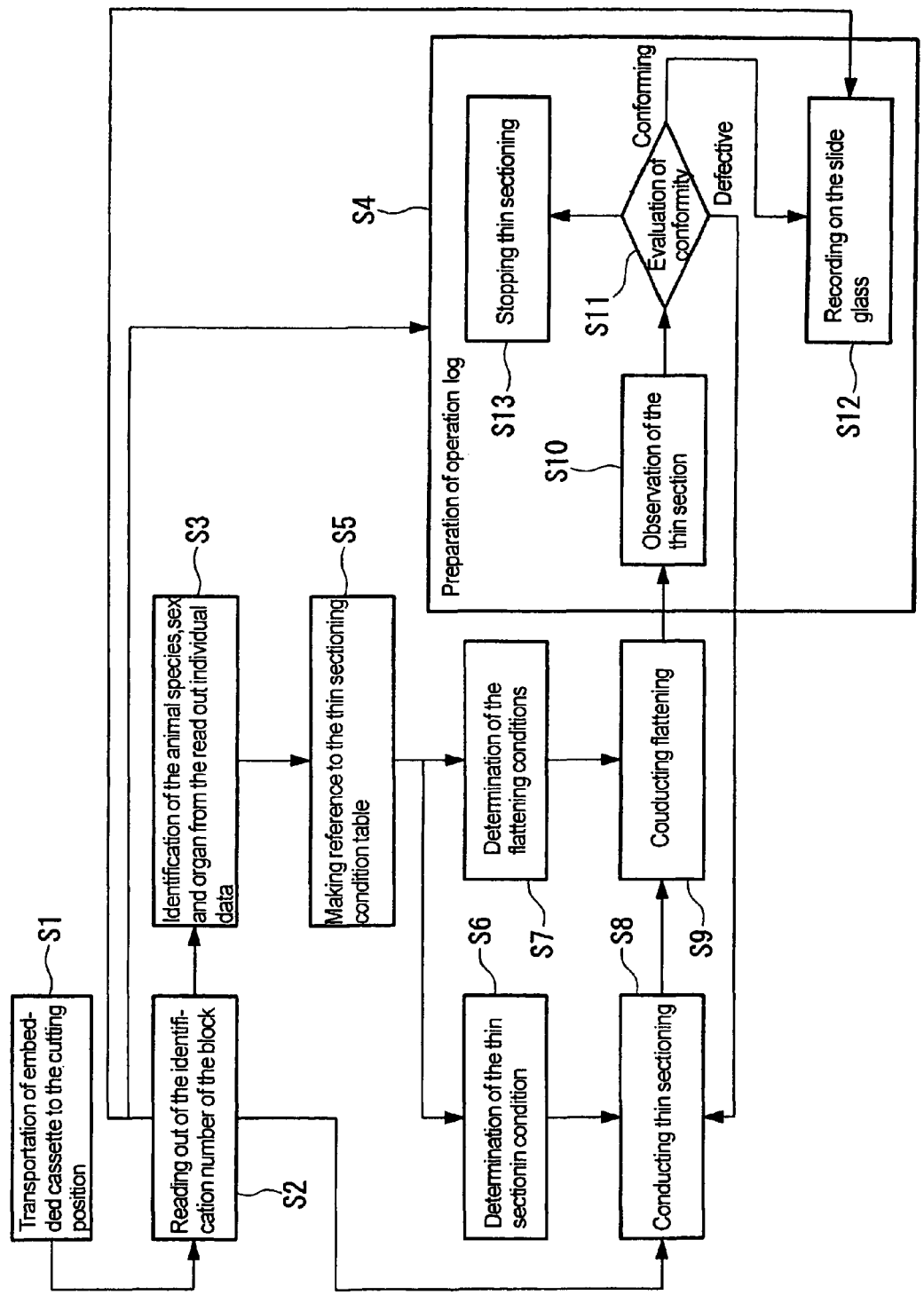
FIG. 7 is a flow chart for manufacturing thin section slide samples using the automatic thin-section slides manufacturing system shown in FIG. 2.

The automated thin-section slides manufacturing method according to the present embodiment, which includes the process steps above, is described in detail below by making reference to the flow chart shown in FIG. 7.

Firstly, the operator stores plural embedded cassettes K, on which different types of embedded blocks B are each mounted, on the storage racks 15 provided inside the cabinet 2. Then, unused slide glasses G are stored in the slide glass storage rack 35. Subsequently, the operator inputs into the condition table 9b of the control part 9 in advance the manufacturing conditions related to the plural embedded cassettes K stored in the cabinet 2; more specifically, the cutting conditions, the flattening conditions, and how many samples to be manufactured, are input in advance in accordance with the type of each biological tissue S.

Upon completion of the initial settings, the manufacturing process for thin section slide samples H is started.

First, the control part 9 runs the first transportation step (S1), in which the block handling robot 3 is controlled as such that the first selected embedded cassette K is taken out from the plurality of embedded cassettes K stored inside the cabinet 2 and transported onto the block fixing table 20, which is the cutting position P. More specifically, the lifting stage 23 and the horizontal stage 25 of the block handling robot 3 are properly operated so that a pair of arms 26a of the clamping robot 26 may be inserted inside the storage rack 15. At this instance, the control part 9 controls the rotation stage 17 at the same time so that it may be rotated properly to make the first embedded block B face to the side of the block handling robot 3.

Then, a pair of arms 26a are operated to bring them nearer to each other, so that they may clamp and fix the embedded cassette K on which the embedded block B is mounted. Subsequently, while keeping the embedded cassette K clamped, the lifting stage 23 and the horizontal stage 25 are properly operated as shown in FIG. 3, so that the embedded cassette K is transported again to the block fixing table 20, and that the embedded cassette K is mounted on the block fixing table 20.

Once the embedded cassette K is mounted on the block fixing table 20 by the first transportation step above, the plane of the embedded block B held in the embedded cassette K is brought into contact by the face with the negatively charged carrier tape 30.

Furthermore, once the embedded cassette K is transported onto the block fixing table 20, which is the cutting position P, the readout part 4 conducts the reading step (S2), in which the individual data D printed on the embedded cassette K is optically read out, and the individual data D thus read out is output to the control part 9.

In this reading step, the control part 9 securely identifies the embedded cassette K out of the plural cassettes by the identification number included in the individual data D. Furthermore, the control part 9 can specify with certainty the type of the embedded block B held in the embedded cassette K from the data (the data showing the type of the laboratory animal, the data showing the sex of the laboratory animal, and the data showing from which organ the sampling was made) provided on the embedded block B included in the individual data D.

Then, the control part 9 conducts the memorizing step (S4), in which the individual data D inclusive of the specified identification number and the data of the embedded block B is memorized in the memory part 9a to prepare an operation log 9c, and at the same time, it refers (S5) to the condition table 9b for the type of the embedded block B. As a result, optimal manufacturing conditions depending on the type of the transported embedded block B are found and determined to carry out the manufacturing under the conditions. That is, the conditions for cutting and flattening are determined (S6, S7). At the same time, the amount of sections to be manufactured is also determined. Then, the control part 9 controls the cutting mechanism 5 and the flattening mechanism 6 to operate under the determined conditions. Furthermore, the control part 9 memorizes the thus determined manufacturing conditions in the memory part 9a simultaneously in the memory step above, so as to prepare the operation log 9c.

After the reading step above, the cutting mechanism 5 cuts the embedded block B being transported onto the block fixing table 20 into sheets by sliding operation of the cutting blade 21. At this instance, the cutting mechanism 5 conducts the cutting (S8) based on the cutting conditions indicated by the control part 9, by controlling at least one selected from the thickness of the thin section B1, the cutting speed, and the cutting angle. Thus, cutting can be carried out under optimal cutting conditions for the biological tissue S embedded in the embedded block B.

Since the embedded block B mounted on the block fixing table 20 is positively charged by an electrifying device, the thin section B1 cut out in the cutting step is adsorbed by the electrostatic force to the lower plane of the carrier tape 30 at the instance it is cut out.

The thin section B1 thus adsorbed is then transported to the water tank 28 of the flattening mechanism 6 together with the carrier tape 30 that is driven by the tape driving mechanism. Once the carrier tape 30 is moved to the upper part of the water tank 28, it is loosened toward the water tank 28, so that it may be immersed in the water W1 reserved in the water tank 28. Thus, the transported thin section B1 becomes immersed in water W1 together with the carrier tape 30, and is set a float on the surface of the water since it is released from the adsorption. Thus, after being floated on the water surface for predetermined duration of time, thin section B1 achieves a flattened state because wrinkles and curls that have generated during cutting can be removed. In this manner, the thin section B1 transported to the flattening mechanism 6 in the second transportation step is flattened by the flattening mechanism 6.

Further, in carrying out the flattening step, the flattening mechanism 6 controls the temperature of water W1 based on the flattening conditions assigned by the control part 9. Moreover, the slide glass handling robot 8, which is to be described hereinafter, scoops up the thin sections B1 floating in the water surface within a set duration of time to complete the flattening.

By thus changing the temperature of water W1 or the flattening time, flattening (S9) can be carried out under the optimal flattening conditions for the biological tissue S embedded in the embedded block B.

On the other hand, as shown in FIG. 6, the slide glass handling robot 8 properly operates the lifting stage 41, the horizontal stage 43 and the slide glass clamping robot 44 in accordance with the cutting out of the thin section B1 and transportation, as such that one unused slide glass G is taken out from the slide glass storage lack 35 and set waiting at the upper side of the water tank 28.

More specifically, the lifting stage 41, the horizontal stage 43, and the slide glass clamping robot 44 are properly operated at first so that a pair of arms 44a of the slide glass clamping robot 44 are inserted into the slide glass storage rack 35. Then, the pair of arms 44a is operated so that they may be brought nearer to each other to clamp and fix one unused slide glass G. Subsequently, while keeping the slide glass G clamped, the lifting stage 41, the horizontal stage 43, and the slide glass clamping robot 44 are properly operated to draw out the slide glass G to move it to the upper side of the water tank 28. This state is kept to wait until a thin section B1 is being transported to the water tank 28.

Then, as the flattening starts when a thin section B1 is transported to the water tank 28 and upon passage of the flattening time determined by the control part 9, the slide glass handling robot 8 properly operates the lifting stage 41, the horizontal stage 43, and the slide glass clamping robot 44, so as to scoop up the floating thin section B1 from the water surface using the clamped slide glass G. In this manner, flattening can be completed within the determined flattening time, and thin section B1 can be transferred on the slide glass G at the same time. Thin section slide sample H is manufactured as a result of the transfer step.

Subsequently, the slide glass handling robot 8 starts transporting the thus manufactured thin section slide samples H towards the storage rack 36 for the thin section slide samples, but the transportation is once stopped at the lower side of the evaluating part 9d and the recording part 10. Then, the evaluating part 9d optically observes (S10) the thin section B1 being clamped by the slide glass handling robot 8, and conducts the evaluation step (S11) in which it is evaluated from the shapes, surface conditions, and the like, that whether or not the manufacturing is conducted in conformity with the manufacturing conditions as determined in the control part 9. Further, the evaluating part 9d sends the evaluation results to the control part 9.

If the evaluating part 9d evaluates it to be in conformity, the control part 9 memorizes the result in the memory part 9a by adding it to the individual data D to be described in the operation log 9c, and at the same time, assigns to the recording part 10 to make a record. On receiving the assignment from the control part 9, the recording part 10 conducts the recording step (S12) by irradiating a laser radiation L to the slide glass G to print the individual data D which includes the identification number memorized in the memory part 9a and the data of the embedded block B.

In this manner, the slide glass G attains a state as such that the same individual data D as that preliminarily printed on the embedded cassette K is recorded thereon. In other words, the thin section slide sample H and the embedded block B held in the embedded cassette K are related to each other.

Upon completion of the recording step, the slide glass handling robot 8 restarts the transportation to store the thin section slide samples H in the storage rack 36 for the thin section slide samples.

On the other hand, in the case the evaluating part 9d evaluates the sample to be defective, the control part 9 memorizes the result in the memory part 9a to describe it in the operation log 9c, and at the same time, it controls as such that a thin section B1 is cut out again from the same embedded block B to manufacture the thin section slide sample H, and that the evaluating part 9d conducts the reevaluation.

In the case the evaluating part 9d evaluates it to be in conformity upon reevaluation, the control part 9 records the result together with the repetition times of reevaluation in the memory part 9a to describe in the operation log 9c. Similar to above, after recording in the recording part 10, the thin section slide sample H is stored inside the storage rack 36 for the thin section slide samples.

In the case the evaluating part 9d do not evaluate as being conforming even after the reevaluation is repeated for predetermined times, the control part 9 stops (S13) the remanufacturing of the thin section slide sample H, and the result is memorized in the memory part 9a to describe in the operation log 9c.

As described above, after completing the manufacturing of the desired number of thin section slide samples H in accordance with the manufacturing conditions from the embedded block B held in the embedded cassette K first transported, the control part 9 controls as such that the block handling robot 3 is operated to return the used embedded cassette K to the cabinet 2 again, and at the same time, controls the block handling robot 3 as such to transport the next selected unused embedded cassette K to the cutting position P. In this manner, the necessary amount of thin sections B1 are cut out consecutively from plural embedded blocks B to continuously manufacture thin section slide samples H.

As a result, necessary amount of thin section slide samples H can be automatically manufactured from the embedded blocks B held in each of the embedded cassettes K, while properly exchanging all the embedded cassettes K stored inside the cabinet 2 without incorporating any manpower.

Accordingly, differing from the conventional ones, the system reduces the burden of the operator while shortening the operation time. Furthermore, it avoids the generation of human errors.

In particular, in accordance with the automatic thin-section slides manufacturing system 1 and the automated thin-section slides manufacturing method of the present embodiment, the manufactured thin section slide samples H are completely related to the original embedded blocks B, because the same individual data D as that of the embedded cassette K are recorded. Thus, quality control of high precision is realized because the operator can easily and surely relate the automatically manufactured thin section slide samples H to the embedded block B from which they were manufactured.

Furthermore, on conducting the recording step, the recording part 10 irradiates laser radiation L to the slide glass G to print the individual data D thereon. That is, printing is effected as if a laser marker is used. Accordingly, clear printing can be realized with minimal application of external force to the slide glass G, thereby preventing deflection, deformation, and the like from occurring on the slide glass G. What is worthy of special mention is that, even if an organic solvent such as xylene and alcohol should be used in the later process steps, the characters printed by the laser radiation remain unerased even if immersed in the organic solvents. Accordingly, extremely reliable thin section slide samples of higher quality can be manufactured.

Further, because a cabinet 2 is provided, the exchange operation of embedded cassettes K can be automatically and efficiently conducted if the operator stores plural embedded cassettes K in the cabinet 2 in advance. Accordingly, the burden of the operator can be further reduced while shortening the operation time.

In addition, because the storage rack 36 for thin section slide samples is provided, the consecutively manufactured thin section slide samples H can be stored automatically. Thus, from this point of view, the burden of the operator can be further reduced while shortening the operation time. Since the finished thin section slide samples H are stored inside the exclusive use rack, the thin section slide samples H can be handled more easily thereafter.

Moreover, the automatic thin-section slides manufacturing system 1 according to the present embodiment comprises a condition table 9b in the control part 9, in which the manufacturing conditions for manufacturing the thin section slide samples H are input in advance. That is, a condition table 9b is provided for optimal manufacturing of the thin section slide samples H depending on the type of the embedded blocks B (more specifically, the type of the embedded biological tissue S) held in each of the embedded cassettes K.

Accordingly, in manufacturing thin section slide samples H, the operator himself need not check the type of the embedded block B, or adjust the manufacturing conditions in advance. From this point of view, the burden of the operator can be reduced and high quality thin section slide samples H can be manufactured.

Since cutting conditions are included in the manufacturing conditions, in the case the biological tissues S differing in hardness, such as liver, bones, and muscles, thin sections B1 can be each cut out under their optimal conditions. Accordingly, the damage on the biological tissues S can be minimized, and high quality thin section slide samples H can be manufactured.

Flattening conditions are also included in the manufacturing conditions. Thus, even when biological tissues S differing in hardness, water absorptivity, and the like, should be processed, flattening can be conducted respectively under their optimal flattening conditions. Thus, the biological tissues S can be surely flattened to manufacture high quality thin section slide samples H.

In the memory part 9a, the identification number of the embedded cassette K, the type, and the manufacturing conditions for the actually transported embedded cassettes K are sequentially accumulated and memorized, and an operation log 9c containing the description is prepared. Accordingly, the operator can easily confirm at a glance the actual operation state and the archives by only confirming the operation log 9c. Thus, quality control of further higher precision can be realized.

In particular, since the evaluation results provided by the evaluating part 9d is added to the individual data D to prepare the operation log 9c, the operator can confirm whether the thin section slide samples H are manufactured in accordance with the manufacturing conditions or not. Thus, the precision of quality control can be further elevated, and at the same time, defective samples can be easily distinguished from the compliant samples.

Furthermore, the control part 9 repeatedly manufactures the thin section slide samples H until the evaluating part 9d evaluates the thus manufactured thin section slide sample H to be conforming. Thus, compliant thin section slide samples H can be produced efficiently in a larger mass.

Further, in the case the evaluation result is still not conforming after repeating the manufacturing for predetermined times, the remanufacturing of the thin section slide sample H from the same embedded block B is discarded, and the results are memorized in the memory part 9a. Accordingly, in the case proper manufacturing is impossible due to some reason, useless operation can be avoided from repeating. Thus, waste of operation time can be avoided and useless consumption of the embedded blocks B can be prevented. Further, the operator can easily specify the causes later because the results are memorized in the memory part 9a.

In addition, by operating the block handling robot 3 on putting in and out the embedded cassettes K stored in one of the storage racks 15, the rotating body 16 can be rotated around the rotation axis L. In this manner, the plural storage racks 15 disposed on the outer periphery can be sequentially faced to the side of the block handling robot 3. Since the storage racks 15 are provided on the outer periphery of the rotating body 16, plural storage racks 15 can be efficiently set in large amounts even in a narrow installation space. Thus, a compact system can be realized. Furthermore, the moving area of the block handling robot 3 under operation for putting in and out the embedded blocks B can be suppressed as much as possible. This also contributes in making the system compact, and enables a simple constitution.

The technical scope of the present invention is not only limited to the embodiments described above, but various modifications can be made so long as they do not deviate from the spirit and the scope of the invention.

For instance, the recording part was so constituted as to irradiate a laser radiation for recording, but is not limited thereto, and any recording method may be used so long as recording can be made on a slide glass. For example, a thermal transfer printer may be used as the recording part, and the individual data may be directly transferred for printing on the slide glass. In this case, the individual data are printable by applying heat and thereby sublimating the ink. Thus, the printing density can be finely adjusted to provide a clear printing. Accordingly, an easily discernible high quality thin section slide samples can be manufactured.

In the case a thermal transfer printer is used, the printing is not only limited to direct printing on the slide glass, and the individual data can be printed on an exclusive use paper, so that the printed exclusive use paper can be attached on the slide glass. In this case again, an easily discernible high quality thin section slide samples can be similarly manufactured.

Furthermore, after the thin section was transferred on the slide glass, the individual data were recorded on the slide glass. However, the case is not limited thereto, and the slide glass may be recorded first, and the thin section may be scooped thereafter from the water tank with the recorded slide glass to manufacture the thin section slide sample.

Further, in the case of manufacturing plural thin section slide samples from the same embedded block according to the embodiment above, the control part may control as such that in the memorizing step, the plural thin section slide samples are distinguished from each other by attaching a branch number to the common individual data and memorized in the memory part, and in the recording step, the recording part may be so controlled that it records the data on the slide glass with the branch number attached.

In this manner, even in the case plural thin section slide samples are manufactured from the same embedded block, they can be clearly distinguished by simply checking the record printed on the slide glass. Furthermore, the operation log can be prepared more accurately. Accordingly, a more accurate quality control can be effected.

Moreover, the explanation was made for the case using the data of the embedded block and the identification number as the individual data to be printed in advance to the embedded cassettes. However, at least the identification number should be printed, and the condition table may be omitted.

However, as described above, preparing both of the individual data and the condition table is more preferred, because not only the embedded cassettes can be related to the thin section slide samples, but also the thin section slide samples can be automatically manufactured under the optimal manufacturing conditions.

Furthermore, a constitution equipped with both the cabinet and the storage rack for thin section slide samples was explained, but only either of them may be provided, or both may be omitted. In such cases, the operator may pass the embedded cassettes to the block handling robot, or the operator may receive the thin section slide samples manufactured by the slide glass handling robot.

However, as described above, it is preferred to equip both of the cabinet and the storage rack for thin section slide samples.

The first transportation unit and the transfer unit were each constituted with a block handling robot and a slide glass handling robot, respectively, but they are not limited to such robots. Further, the thin sections were adsorbed onto the carrier tape using static electricity, and the second transportation unit was constituted as such that the thin sections may be transported by the carrier tape; however, the constitution is not only limited thereto.

Figure 8:
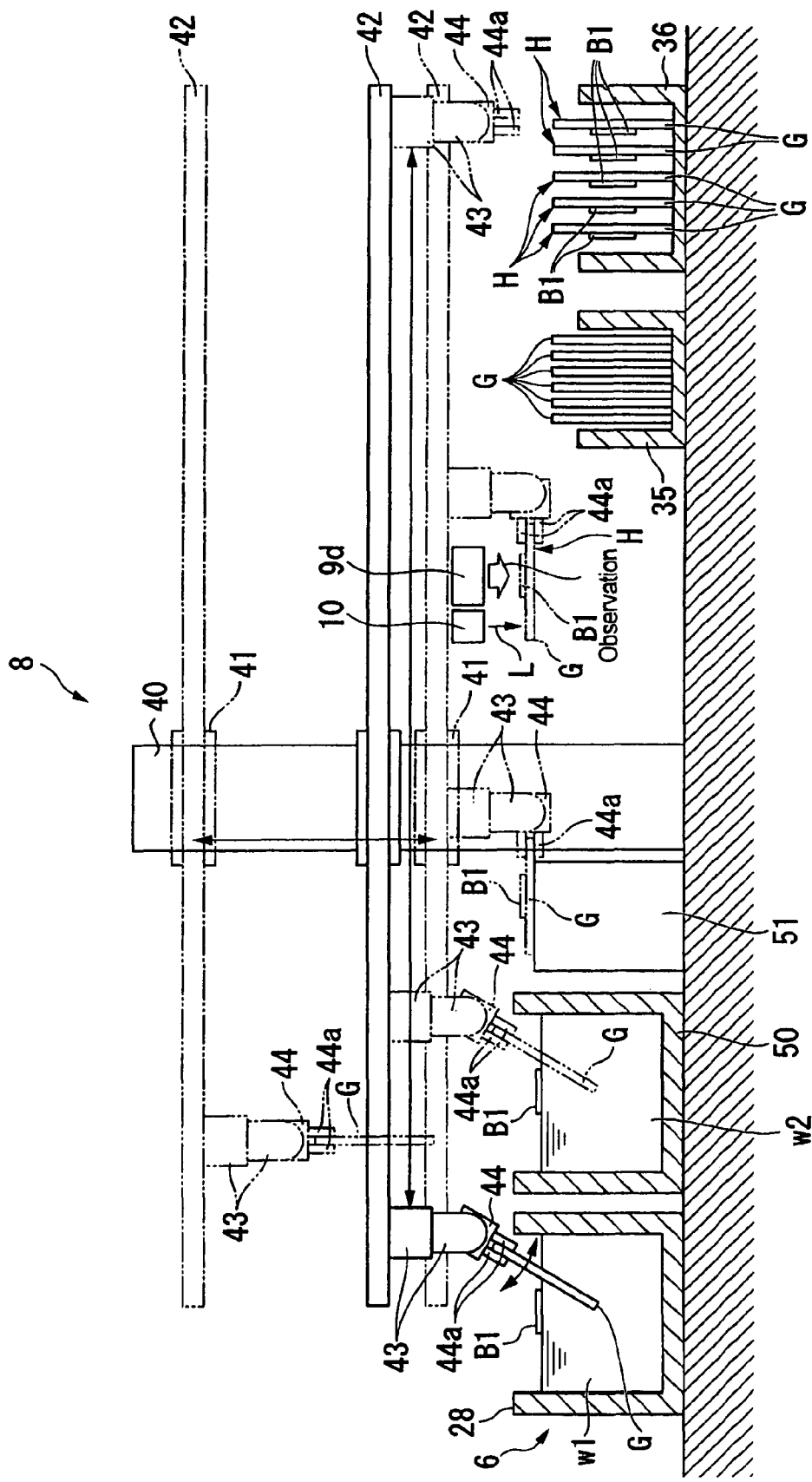
FIG. 8 is a diagram showing another example of a flattening unit as shown in FIG. 6, which is capable of carrying out water flattening, hot water flattening, and hot plate flattening.

In the embodiment above, the flattening mechanism was constituted simply by a water tank containing water, but is not only limited thereto. For instance, as shown in FIG. 8, the flattening mechanism 6 may have a second water tank containing hot water W2 in the neighbor of the water tank 28, and a hot plate 51.

In this case, the slide glass handling robot 8 mounts the water-flattened thin section B1 on the slide glass G, and the thin section B1 is transported to the second water tank and set a float in hot water (liquid) W2. Since the hot water flattening makes the thin section B1 more easily extended, wrinkles, curls, and the like which remain unremoved by the water W1 flattening can be removed. Thus, thin section slide samples H of higher quality can be manufactured. In this case, the second transportation step refers to the process until the thin section B1 is set a float in hot water W2.

Subsequent to the hot water flattening, by mounting the slide glass G together with the thin section B1 mounted thereon on a hot plate 51, heat can be applied to the thin section B1 through the slide glass G. In this manner, wrinkles, curls, and the like which remain unremoved in hot water flattening can be removed.

Thus, the use of the second water tank 50 and the hot plate 51 is more preferred, because thin section slide samples H with higher quality can be manufactured.

Also preferred is to input, as the flattening conditions to the condition table 9b, whether hot water W2 is used or not, whether hot plate 51 is used or not, and the time duration of their use.

The automatic thin-section slides manufacturing system and the automated thin-section slides manufacturing method according to the invention reduce the burden of operators, which automatically manufacture required number of thin section slide samples from plural embedded blocks, and, at the same time, completely relate the manufactured thin section slide samples to the original embedded blocks to enable quality control at high precision.

What is claimed is:

1. An automatic thin-section slide sample manufacturing system for manufacturing thin-section slide samples respectively from a plurality of embedded blocks containing a biological sample embedded therein with an embedding medium and held in an embedded cassette having imprinted thereon individual data including at least an identification number, the automatic thin-section slides manufacturing system comprising:
   a first transportation unit that transports an arbitrarily selected embedded cassette from the plurality of embedded cassettes to a cutting position;
   a cutting unit that, after the embedded cassette is transported to the cutting position, cuts the embedded block to provide sheet-like thin sections with a predetermined thickness;
   a readout unit that reads out the individual data when the embedded cassette is transported to the cutting position;
   a flattening unit that flattens each of the thin sections, the flattening unit comprising a storage tank containing a liquid stored therein;
   a second transportation unit that transports the thin sections cut out by the cutting unit to the storage tank and sets them afloat on a surface of the liquid stored in the storage tank;
   a transfer unit that prepares the thin section slide samples by transferring onto a substrate the thin sections flattened by the flattening unit;
   a control unit comprising a memory part that stores the individual data read out by the readout unit, and a condition table into which is input manufacturing conditions for manufacturing the thin section for each of the plurality of embedded cassettes;
   an evaluation unit that observes and evaluates whether or not the thin sections are prepared in accordance with the manufacturing conditions input in the condition table; and
   a recording unit that records on the substrate the individual data stored in the memory part in accordance with an instruction from the control unit.

2. An automatic thin-section slide sample manufacturing system as claimed in claim 1; wherein the control unit is configured to issue an instruction to the recording unit when a plurality of the thin section slide samples are prepared from the same embedded block, so that the memory part stores the individual data in such a state that branch numbers for respectively distinguishing the thin section slide samples are each added to the individual data and that the data is recorded on the substrates.

3. An automatic thin-section slide sample manufacturing system according to claim 1; further comprising a cabinet for storing the plurality of embedded cassettes; wherein the control unit is configured to control the first transportation unit such that an arbitrarily selected embedded cassette is taken out from the cabinet and transported to the cutting position and, after the necessary amount of thin sections is cut out, the embedded cassette is returned back to the cabinet to take out a next embedded cassette.

4. An automatic thin-section slide sample manufacturing system according to claim 3; wherein the manufacturing conditions are cutting and flattening conditions that are input into the condition table.

5. An automatic thin-section slide sample manufacturing system according to claim 1; wherein the manufacturing conditions are cutting and flattening conditions that are input into the condition table.

6. An automatic thin-section slide sample manufacturing system as claimed in claim 1; wherein the recording unit records the individual data onto the substrate by irradiating laser radiation.

7. An automatic thin-section slide sample manufacturing system as claimed in claim 1; wherein the recording unit comprises a thermal transfer printer that prints the individual data by transferring the individual data onto the substrate.

8. An automatic thin-section slide sample manufacturing system as claimed in claim 1; wherein the recording unit comprises a thermal transfer printer that transfers the individual data to a paper that is attached to the substrate.

9. An automatic thin-section slide sample manufacturing system as claimed in claims 1; wherein the transfer unit comprises a storage rack that stores plurality of thin-section slide samples; and wherein the control unit controls the transfer unit in such a manner that the manufactured thin-section slide samples are stored in the storage rack.

10. An automated thin-section slide sample manufacturing method for manufacturing thin-section slide samples respectively from a plurality of embedded blocks containing a biological sample embedded therein with an embedding medium and held in an embedded cassette having imprinted thereon individual data including at least an identification number, the method comprising:
   a first transportation step for transporting the embedded cassette arbitrarily selected from the plurality of embedded cassettes to a cutting position;
   a reading step for reading the individual data from the embedded cassette transported to the cutting position;
   a storing step for storing into a memory part the individual data read out in the reading step;
   a cutting step for cutting out a sheet-like thin section with a predetermined thickness from the embedded block transported to the cutting position;
   a second transportation step for transporting the cut thin section to a storage tank filled with a liquid and setting the cut thin section afloat on a surface of the liquid to flatten the cut thin section;
   a transfer step for transferring the flattened thin section onto a substrate to manufacture the thin-section slide sample;
   an observation and evaluation step for observing and evaluating whether or not the thin-section slide sample is prepared in accordance with predetermined manufacturing conditions input into a condition table into for manufacturing the thin sections for each of the plurality of embedded cassettes; and
   a recording step for storing the individual data in the memory part and for recording the stored individual data unto the substrate in accordance with a result of the observation and evaluation step.

11. An automated thin-section slide sample manufacturing method as claimed in claim 10; wherein in the recording step, when a plurality of the thin section slide samples are prepared from the same embedded block, the individual data is stored in such a state that branch numbers for respectively distinguishing the thin section slide samples are each added to the individual data and the individual data is recorded on the substrates.

12. An automatic thin-section slide sample manufacturing method according to claim 10; further comprising: a storing step of storing the plurality of embedded cassettes in a cabinet; and a control step for controlling the first transportation step such that an arbitrarily selected embedded cassette is taken out from the cabinet and transported to the cutting position and, after the necessary amount of thin sections is cut out, the embedded cassette is returned back to the cabinet to take out a next embedded cassette.

13. An automatic thin-section slide sample manufacturing method according to claim 12; wherein the manufacturing conditions are cutting and flattening conditions.

14. An automatic thin-section slide sample manufacturing system according to claim 10; wherein the manufacturing conditions are cutting and flattening conditions.

15. An automated thin-section slide sample manufacturing method as claimed in claim 10; wherein the recording step comprises the step of recording the individual data onto the substrate by irradiating laser radiation.

16. An automated thin-section slide sample manufacturing method as claimed in claim 10; wherein the recording step comprises the step of transferring the individual data onto the substrate using a thermal transfer printer.

17. An automated thin-section slide sample manufacturing method as claimed in claim 10; wherein the recording step comprises the step of transferring the individual data onto a paper attached to a substrate using a thermal transfer printer.

18. An automated thin-section slide sample manufacturing method as claimed in claims 10; wherein the transfer step comprises the step of storing the manufactured thin-section slide sample in a storage rack configured for storing a plurality of thin-section slides.

19. An automatic thin-section slide sample manufacturing system for manufacturing thin-section slide samples from respective embedding blocks containing a biological sample embedded therein with an embedding medium and held in an embedding cassette having imprinted thereon individual data including at least an identification number, the system comprising:
first conveyance means for conveying an embedding cassette to a cutting position;
cutting means for cutting an embedding block into sheet-like thin sections with a predetermined thickness after the embedding cassette is transported to the cutting position;
readout means for reading out the individual data when the embedding cassette is transported to the cutting position;
flattening means for flattening each of the thin sections;
second conveyance means for conveying each of the cut thin sections to the flattening means;
transferring means for transferring each of the flattened thin sections onto a substrate to form a thin-section slide sample;
control means comprising memory means for storing the individual data read out by the readout means and a condition table into which is input manufacturing conditions for manufacturing the thin sections;
evaluation means for observing and evaluating whether or not each of the thin sections is prepared in accordance with the manufacturing conditions input in the condition table; and
recording means for recording onto the substrate the individual data stored in the memory part in accordance with an instruction from the control means.

20. An automatic thin-section slide sample manufacturing system according to claim 19; wherein the manufacturing conditions are cutting and flattening conditions that are input into the condition table.

* * * * *